(12) United States Patent
Costa et al.

(10) Patent No.: US 6,932,186 B2
(45) Date of Patent: Aug. 23, 2005

(54) STETHOSCOPE WITH REMOVABLE LIGHT ASSEMBLY

(75) Inventors: Richard Costa, Bedminster, NJ (US); Hung Mach, Flushing, NY (US); Matthew T. Coe, Annandale, NJ (US)

(73) Assignee: Pharma Design Inc, Warren, NJ (US)

( * ) Notice: Subject to any disclaimer, the term of this patent is extended or adjusted under 35 U.S.C. 154(b) by 0 days.

(21) Appl. No.: 10/637,839

(22) Filed: Aug. 8, 2003

(65) Prior Publication Data

US 2005/0029038 A1 Feb. 10, 2005

(51) Int. Cl.[7] .......................... A61B 7/02; F21V 33/00; F21V 21/088; F21L 4/04
(52) U.S. Cl. ....................... 181/131; 362/109; 362/200; 362/396; 600/528
(58) Field of Search ................... 181/131, 129, 181/141; 362/109, 132, 105, 119, 102, 200, 201, 396; D24/134, 133; 600/528, 527, 200, 199; 381/67; D26/39, 38, 60

(56) References Cited

U.S. PATENT DOCUMENTS

| | | | | |
|---|---|---|---|---|
| 1,287,393 A | * | 12/1918 | Molnar | 362/200 |
| 4,307,539 A | * | 12/1981 | Klein | 446/472 |
| 5,228,774 A | * | 7/1993 | Liao | 362/396 |
| 5,448,459 A | * | 9/1995 | Rogers | D26/60 |
| 5,469,343 A | * | 11/1995 | Speck | 362/102 |
| 5,584,567 A | * | 12/1996 | Rumpel | 362/396 |
| 5,632,552 A | * | 5/1997 | Wang et al. | 362/396 |
| 5,663,533 A | * | 9/1997 | Judge | 181/131 |
| 5,785,408 A | * | 7/1998 | Tseng | 362/119 |
| 5,797,670 A | * | 8/1998 | Snoke et al. | 362/119 |
| 5,989,186 A | * | 11/1999 | Alatriste | 181/131 |
| 6,176,600 B1 | * | 1/2001 | Huang | 362/396 |
| 6,202,784 B1 | * | 3/2001 | Alatriste | 181/131 |
| 6,299,323 B1 | * | 10/2001 | Yu et al. | 362/200 |
| 6,341,881 B1 | * | 1/2002 | Huang | 362/396 |
| 6,428,180 B1 | * | 8/2002 | Karram et al. | 362/119 |
| 6,454,045 B1 | * | 9/2002 | Ryan | 181/131 |
| 6,508,580 B2 | * | 1/2003 | Collins | 362/396 |
| 6,598,995 B2 | * | 7/2003 | Huang | 362/396 |
| 6,682,208 B1 | * | 1/2004 | Pan | 362/396 |
| 6,726,344 B2 | * | 4/2004 | Lee | 362/396 |
| D490,923 S | * | 6/2004 | Costa et al. | D26/39 |
| 2002/0159253 A1 | * | 10/2002 | Dalebout et al. | 362/102 |

* cited by examiner

Primary Examiner—Edgardo San Martin
(74) Attorney, Agent, or Firm—Watov & Kipnes, P.C

(57) ABSTRACT

A light transmitting device for attachment to a stethoscope headpiece which provides for reversible engagement of the device to the headpiece so that the same can be removed such as for repairs or replacement of batteries. The transmitting device provides a source of light without interfering with the operation of the stethoscope and can be provided without retooling the stethoscope to accommodate a source of light.

3 Claims, 6 Drawing Sheets

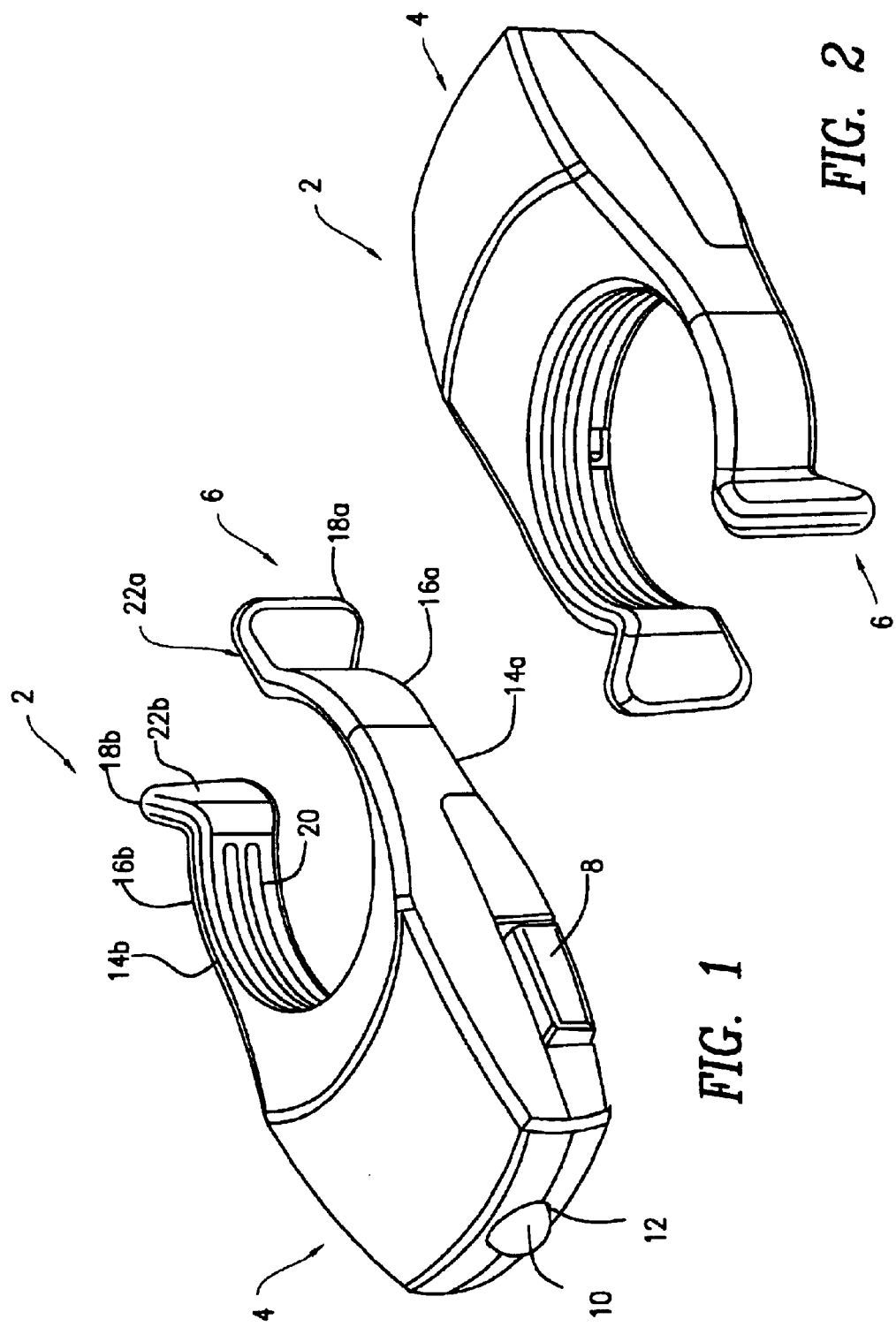

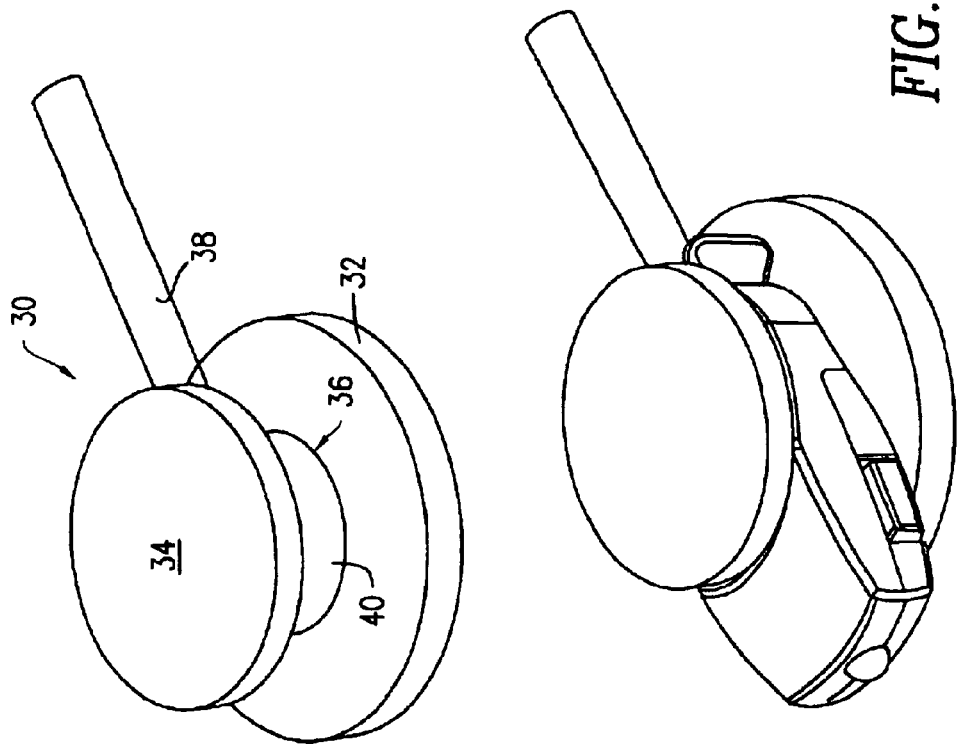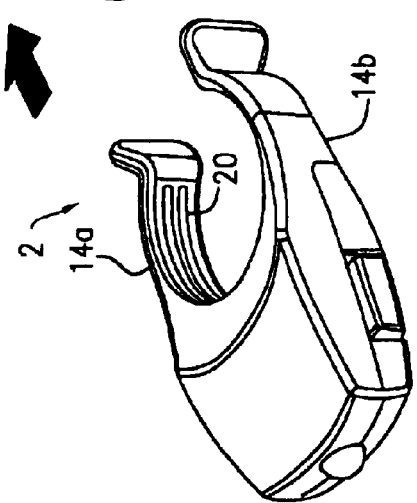

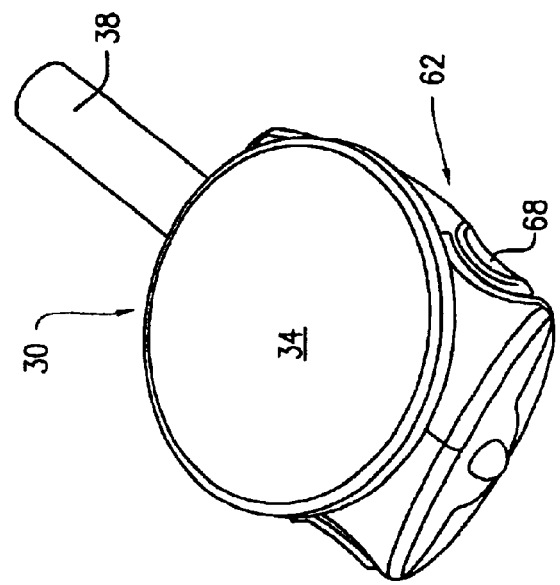
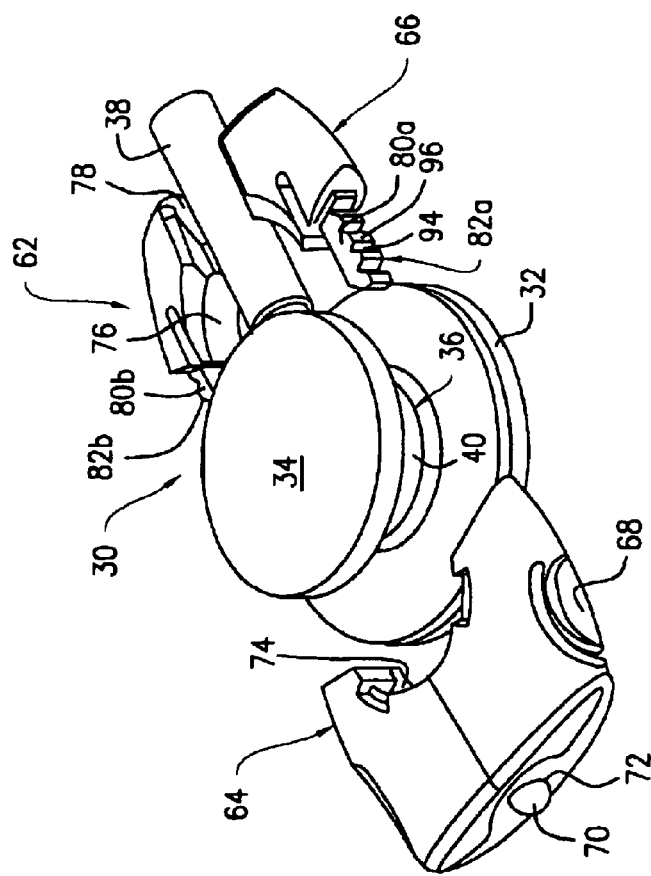
FIG. 8
FIG. 7

STETHOSCOPE WITH REMOVABLE LIGHT ASSEMBLY

FIELD OF THE INVENTION

The present invention is generally directed to a light transmitting assembly which may be reversibly attached to the headpiece of a stethoscope to provide a readily accessible light source when needed and which provides the ability to remove the light transmitting assembly when not needed.

BACKGROUND OF THE INVENTION

It is known in the art to provide attachments to a stethoscope to enable a doctor to employ various devices that may be used during the course of conducting an examination of a patient when a stethoscope is needed as part of the examination.

One such example is disclosed in Wehby (U.S. Pat. No. 2,566,687) in which a stethoscope head is constructed with a flashlight, tongue blade and thermometer to produce a comprehensive stethoscope type of apparatus. Such devices are disadvantageous because the stethoscope head must be retooled at significant costs and the resulting stethoscope, although having the additional features set forth in the reference, must be produced at significantly higher cost in order to accommodate all of the medical devices within the head of the stethoscope.

There have been stethoscopes provided with a light source which do not include other medical functions. One such example is disclosed in Aratriste (U.S. Pat. No. 5,989,186) which includes a stethoscope head and flexible tubing coupled to the stethoscope head and in communication with ear pieces for the transmission of sound from the patient's body. A casing is affixed to a cover of the stethoscope head and has a light source mounted therein. Quite clearly, as with the '687 patent reference, significant modification of a standard stethoscope especially the headpiece must be made in order to accommodate the light source part in the '186 patent reference.

Another example of a stethoscope with a light source is disclosed in Ryan (U.S. Pat. No. 6,454,045) which employs an optical fiber light through the tubing that connects the ear pieces to the stethoscope head. Hereagain, such a device requires significant retooling of the standard stethoscope and although providing a suitable light source, it does so at a significant increase in cost.

It would therefore be desirable for use with a standard stethoscope to have a light source which is reversibly attachable to the headpiece of the stethoscope which can be used as desired and readily removed when not needed.

It would be a further advantage in the art of providing a stethoscope with a light source to enable the light resource to be readily accessible to have component parts such as light bulbs and batteries easily replaced without having to involve a stethoscope itself in the repair process.

SUMMARY OF THE INVENTION

The present invention is generally directed to a light transmitting device for attachment to a stethoscope headpiece which can be easily attached to the headpiece and removed therefrom as needed such as when repairs are desired.

In one aspect of the present invention, there is provided a light transmitting device for attachment to a stethoscope headpiece comprising:

a housing having a forward end and a rearward end, said rearward end comprising a pair of spaced apart opposed arms defining a space therebetween for releasably receiving a portion of the stethoscope headpiece in reversible locking engagement, said forward end containing a light transmitting assembly and means for selectively activating the light transmitting assembly to thereby generate and transmit light while the light transmitting device is in locking engagement with the stethoscope headpiece.

BRIEF DESCRIPTION OF THE DRAWINGS

The following drawings in which like reference characters indicate like parts are illustrative of embodiments of the invention and are not intended to limit the invention as encompassed by the claims forming part of the application.

FIG. 1 is a perspective view of an embodiment of the light transmitting device of the present invention;

FIG. 2 is a rear view of the light transmitting device shown in FIG. 1;

FIG. 4 is a perspective view showing the light transmitting device of FIG. 1 prior to engagement with the headpiece of a stethoscope;

FIG. 5 is a perspective view of the light transmitting device shown in locking engagement with the headpiece of a stethoscope;

FIG. 7 is a perspective view showing a light transmitting device in a second embodiment of the present invention prior to engagement with the headpiece of a stethoscope;

FIG. 8 is a perspective view of the light transmitting device of FIG. 7 shown in locking engagement with the headpiece of a stethoscope.

DETAILED DESCRIPTION OF THE INVENTION

Figure 3:
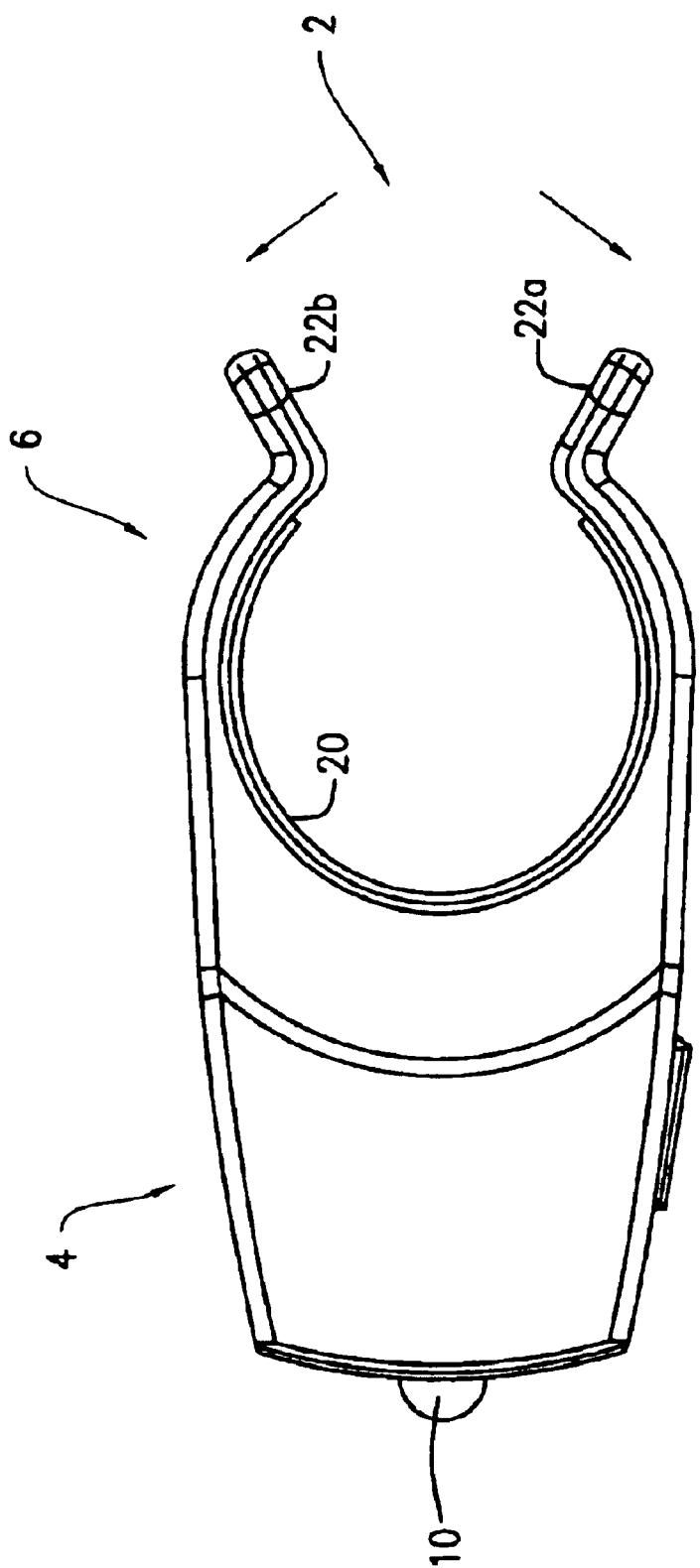
FIG. 3 is a top view of the light transmitting device shown in FIG. 1.

The present invention is generally directed to a light transmitting assembly which is reversibly attachable to the headpiece of a stethoscope. The device can be easily attached to the headpiece of the stethoscope and can be easily activated to emit a light beam to assist medical personnel in performing medical functions such as those associated with use of a stethoscope. When the light transmitting device is no longer of use, or is in need of repairs, it can be easily removed from the headpiece of the stethoscope.

Referring to the drawings and particularly to FIGS. 1 and 2, there is shown a light transmitting device 2 for attachment to a stethoscope headpiece (See FIGS. 4 and 5). The light transmitting device 2 has a forward portion 4 and a rearward portion 6. The forward portion 4 contains a light transmitting assembly as described hereinafter which includes a light transmitting activator 8 in the form of an on/off switch which can ultimately be turned on and off by pressing thereon with a finger such as the thumb. A beam of light emanates from the light transmitting assembly through a bulb 10 partially extending from the forward portion 4 through an opening 12.

The rearward portion 6 of the light transmitting device 2 is adapted to releasably engage the headpiece of a stethoscope as discussed hereinafter in connection with FIG. 4.

The rearward portion 6 is comprised of a pair of spaced apart arms 14a and 14b. The arms 14a and 14b comprise an inner portion 16a and 16b and an outer portion 18a and 18b. The inner portion 16a, 16b of respective arms 14a, 14b are in a spaced apart relationship which enables the arms 14a and 14b to engage in reversible locking engagement with the head of the stethoscope. In the embodiment shown in FIGS. 1 and 2, the inner portion 16a and 16b have the respective arms 14a and 14b form a curvilinear, essentially circular inner surface 20 which is tailored to fit around a corresponding substantially circular surface of the headpiece of the stethoscope as explained hereinafter.

The outer portions 18a and 18b of the arms 14a and 14b extend at an angle from the respective inner portion 16a and 16b so that the outer portions 18a and 18b may serve as clips to disengage the arms from the headpiece of the stethoscope. In the embodiments shown in FIGS. 1 and 2, the outer portions 18a and 18b have respective inner surfaces 22a and 22b which when forced in opposite directions can release the light transmitting device from contact with the headpiece of the stethoscope so that it may be removed therefrom. This operation is best shown in FIG. 3 wherein the user may apply pressure to the inner surfaces 22a and 22b in the direction of the respective arrows thereby forcing the inner surfaces 22a and 22b further away from each other so that the inner surface 20 is released from locking engagement with the corresponding surface of the headpiece of the stethoscope.

The light transmitting device of the present invention may be secured to the stethoscope headpiece as shown in FIG. 4. As shown therein the stethoscope headpiece 30 comprises a base 32 for placing against the patient's skin and a holder 34 between the base 32 and the holder 34 is a neck portion 36 which provides operative contact with a tube 38 which enables sound to travel from the base 32 to the medical personnel's ears for an ear piece (not shown) in a conventional manner. The neck portion 36 has an exterior surface 40 which is shown in FIG. 4 as being curvilinear. It will be understand that the neck portion 36 may have other shapes such as a square, rectangle, polygon and the like.

In the embodiment shown in FIG. 4, the neck portion has a curvilinear surface 40 which is conventional for headpieces typically associated for use with stethoscopes. As shown in FIG. 4, the light transmitting device 2 has an inner surface 20 which has the same curvilinear shape as the surface 40 of the neck portion 36. When it is desirable to attach the light transmitting assembly 22 to the neck portion 36 of the headpiece 30, the user aligns the arms 14a and 14b with the neck portion 36 and then moves the light transmitting device into position as shown in FIG. 5. The arms 14a and 14b will flex about the neck portion 36 and be secured thereto in reversible locking engagement as shown in FIG. 5.

When it is desirable to remove the light transmitting device from operable contact with the headpiece 30, the user moves the arms 14a and 14b away from each other by moving the same away from each other as shown and described in connection with FIG. 3. The arms 14a and 14b are thereby able to disengage from the neck portion 36 so that the light transmitting device 2 is released from operable engagement to the headpiece.

Figure 6:
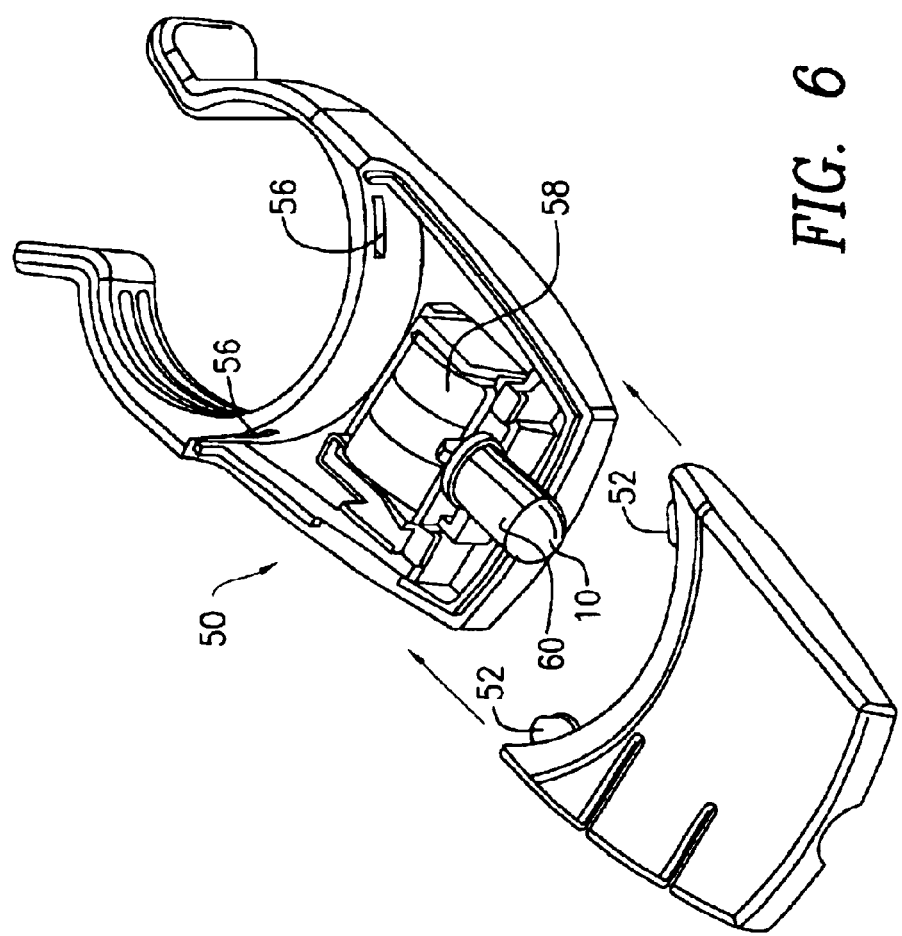
FIG. 6 is a perspective view of the light transmitting assembly contained within the light transmitting device.

The light transmitting device 2 contains within the forward portion 4 a light transmitting assembly. Access to the light transmitting assembly 50 in the forward portion 4 is via a cover 52 which may be secured to the light transmitting device 2 in a variety of ways. As specifically shown in FIG. 6, a cover has a pair of projections which are adapted to reversibly secure the cover 52 through corresponding slots 56.

The light transmitting assembly 50 includes a power source 58 such as one or more batteries and a bulb 10 which is secured in a protective casing 60. Whereas provided between the power source 58 and the bulb 10 a conventional electrical connection which enables electrical power to be provided to the bulb to light the bulb when desired. The light transmitting activator 8 (as shown best in FIG. 1) enables control operable contact between the power source 58 and the bulb 10 shown in FIG. 6 so that the presence or absence of light through the bulb 10 is controlled by the user of the device.

With reference to FIGS. 7 and 8, there is shown as a second embodiment of the present invention a light transmitting device indicated generally by reference numeral 62. The light transmitting device 62 provides an easy and effective means of providing a light source in proximity to the head of a stethoscope in a manner similar to the light transmitting device 2 of FIG. 1. The light transmitting device 62 is generally composed of a two piece interlocking structure which can be readily disassembled and re-assembled for securing engagement with the headpiece 30 of a stethoscope as will be further described hereinafter. The light transmitting device 62 has a forward component 64 and a rearward component 66 operatively associated with one another. The forward component 64 contains a light transmitting assembly as further described hereinafter which includes a light transmitting activator 68 in the form of an on/off switch which can be turned on and off by pressing thereon with a finger such as the thumb. A beam of light is emitted from the light transmitting assembly through a bulb 70 shown partially extending from the forward component 64 through an opening 72.

The rearward component 66 of the light transmitting device 62 is designed to engage and couple with the forward component 64 to form an enclosure, preferably an adjustable enclosure, around the neck portion 36 of the headpiece 30. The enclosure formed by the coupling of the forward and rearward components 64 and 66 securely attaches the light transmitting device 62 to the stethoscope headpiece 30 as shown best in FIG. 8.

Referring back to FIG. 7, the forward component 64 includes a curved inside surface 74 which is adapted to at least substantially conform to the curvilinear shape of the surface 40 of the neck portion 36. The rearward component 66 includes a curved inner surface 76 which is which is adapted to at least substantially conform to the curvilinear shape of the surface 40 of the neck portion 36 on the opposite side from the forward component 64. The rearward component 66 includes a groove 78 for accommodating the stethoscope tube 38, and a pair of spaced apart arms 80a and 80b for engagement with the forward component 64. The arms 80a and 80b each comprise a serrated outer portion 82a and 82b comprised of alternating projections 94 and furrows 96. Each of the arms 80a and 80b extends along one side of the stethoscope neck portion 36 to initiate a reversible locking engagement with the forward component 64 as will be explained hereinafter. The arms 80a and 80b enable the light transmitting device 62 to accommodate varying diameters of the headpiece 30 of the stethoscope by allowing the first and second components 64 and 66 to be moved away or toward each other as required for providing secure attachment thereon.

Figure 9:
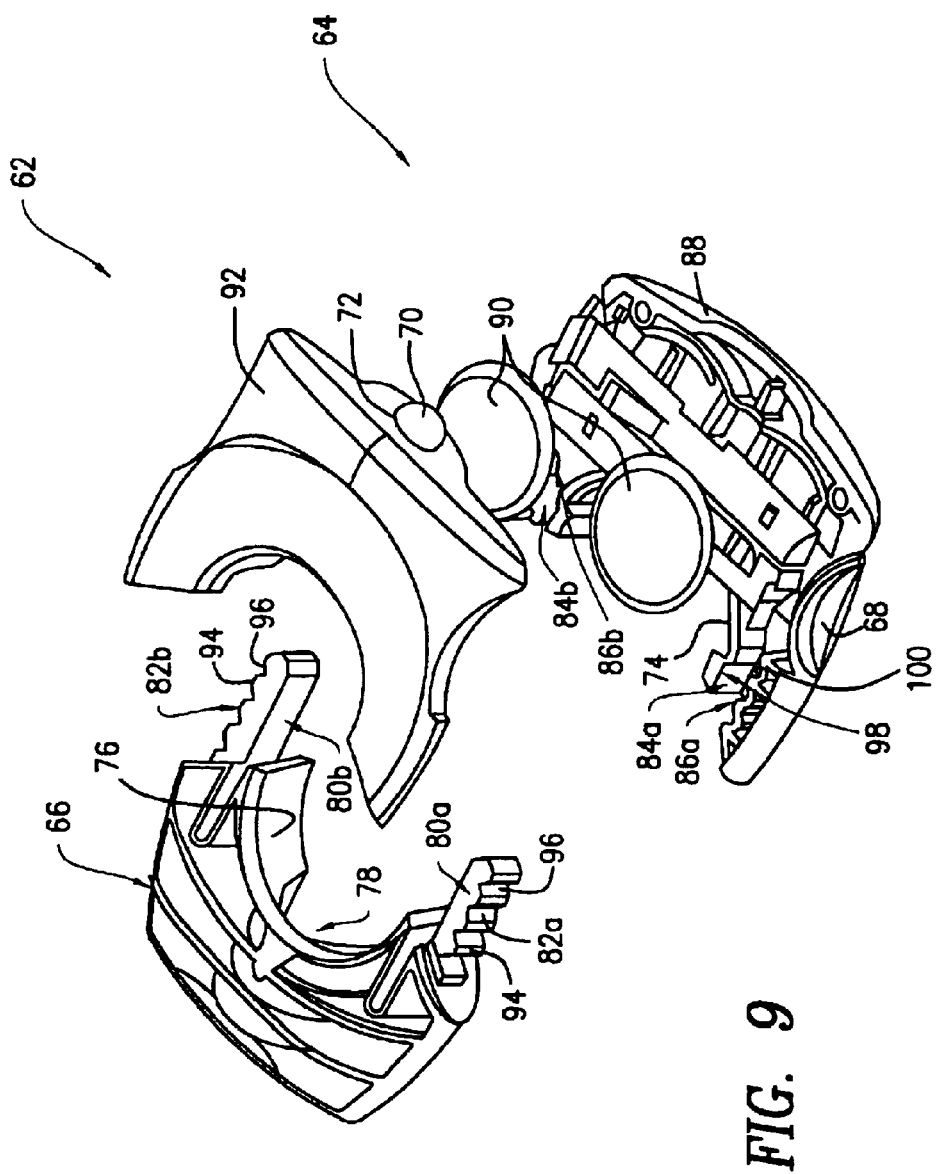
FIG. 9 is a bottom perspective view showing the exploded assembly detail of the light transmitting device.

With reference to FIG. 9, the forward component 64 includes a pair of slots 84a and 84b which are correspondingly positioned to reversibly receive and retain therein the associated arms 80*a* and 80*b*. The slots 84*a* and 84*b* include serrated inside surfaces 86*a* and 86*b* including corresponding projections 98 and furrows 100 which are adapted to interact with the serrated outer portions 82*a* and 82*b*, and their corresponding projections 94 and furrows 96 of the arms 80*a* and 80*b*, respectively, to provide adjustable frictional contact and retainment. When it is desirable to remove the light transmitting device 62 from operable contact with the headpiece 30, the forward and rearward components 64 and 66 can be pulled apart and away from each other. The arms 80*a* and 80*b* of the rear component 66 are thereby able to disengage from the slots 84*a* and 84*b* of the forward component 64 so that the light transmitting device 62 is released from operable engagement to the stethoscope headpiece 30 of the stethoscope. The presence of several adjacent pairs of projections 94 and furrows 96 on the arms 80*a* and 80*b* and corresponding projections 98 and furrows 100 of the inside surfaces 86*a* and 86*b* of the slots 84*a* and 84*b*, respectively enables the forward components rearward components 64 and 66 to be secured about the headpiece 30 over a range of widths and sizes.

The light transmitting device 62 contains within the forward component 64 a light transmitting assembly. Access to the light transmitting assembly (not shown) in the forward component 64 is via a cover 88 which may be secured to the light transmitting device 62 in a variety of ways. The light transmitting assembly generally comprises the same components including a power source 90 such as one or more batteries and a bulb 70 which is secured in a protective casing 92 as similarly described for the light transmitting device 2. Whereas provided between the power source 90 and the bulb 70 a conventional electrical connection which enables electrical power to be provided to the bulb to light the bulb when desired. The light transmitting activator 68 enables control over the operable contact between the power source 90 and the bulb 70 so that the presence or absence of light through the bulb 70 is controlled by the user of the device.

The light transmitting device of the present invention may be constructed from a variety of materials, preferably a sturdy but flexible plastic material such as polyethylene, polypropylene, polystyrene, acrylonitrile butadiene styrene (ABS) and the like.

What is claimed is:

1. A light transmitting device for attachment to a stethoscope headpiece comprising:

a housing having a forward end and a rearward end, said rearward end comprising a pair of spaced apart opposed arms extending substantially in the same plane away from said housing and defining a space therebetween for releasably receiving a portion of the stethoscope headpiece in reversible locking engagement, said forward end containing a light transmitting assembly and means for selectively activating the light transmitting assembly to thereby transmit light in substantially the same plane as the opposed arms while the light transmitting device is in locking engagement with the stethoscope headpiece.

2. The light transmitting device of claim 1 wherein the means for selectively activating assembly may be activated while the light transmitting device is disengaged from the stethoscope headpiece.

3. The light transmitting device of claim 1 wherein the spaced apart opposed arms are made of a flexible material which apply pressure to the stethoscope headpiece while in locking engagement to thereby secure the light transmitting device to the headpiece.

* * * * *